(12) United States Patent
D'Antonio (10) Patent No.: US 10,973,271 B2
(45) Date of Patent: Apr. 13, 2021

(54) BRA GAUGING DEVICE

(71) Applicant: Gregg D'Antonio, Mount Laurel, NJ (US)

(72) Inventor: Gregg D'Antonio, Mount Laurel, NJ (US)

(*) Notice: Subject to any disclaimer, the term of this patent is extended or adjusted under 35 U.S.C. 154(b) by 154 days.

(21) Appl. No.: 16/529,623

(22) Filed: Aug. 1, 2019

(65) Prior Publication Data
US 2020/0054087 A1    Feb. 20, 2020

Related U.S. Application Data

(60) Provisional application No. 62/719,491, filed on Aug. 17, 2018.

(51) Int. Cl.
| | |
|---|---|
| *A41H 1/02* | (2006.01) |
| *G01B 3/1061* | (2020.01) |
| *G01B 3/1084* | (2020.01) |
| *G01B 3/1071* | (2020.01) |
| *G01B 3/1003* | (2020.01) |
| *G01B 3/1092* | (2020.01) |
| *A61B 5/107* | (2006.01) |

(52) U.S. Cl.
CPC ............. *A41H 1/02* (2013.01); *G01B 3/1004* (2020.01); *G01B 3/1061* (2013.01); *G01B 3/1071* (2013.01); *G01B 3/1084* (2013.01); *A61B 5/107* (2013.01); *G01B 3/1092* (2020.01); *G01B 2003/1064* (2013.01); *G01B 2003/1066* (2013.01); *G01B 2003/1079* (2013.01)

(58) Field of Classification Search
CPC ...... A41H 1/02; G01B 3/1004; G01B 3/1071; G01B 3/1084; G01B 2003/1064; G01B 2003/1066; G01B 2003/1079; A61B 5/107; A61B 5/1072; A61B 5/1073
USPC .................................. 33/512, 1 BB, 2 R, 1 V
See application file for complete search history.

(56) References Cited

U.S. PATENT DOCUMENTS

| | | | | |
|---|---|---|---|---|
| 2,559,501 | A * | 7/1951 | Graf ......................... | A41H 1/02 33/2 R |
| 2,575,343 | A * | 11/1951 | Heiman ................... | A41H 1/02 33/2 R |
| 2,725,633 | A * | 12/1955 | Graf ....................... | A61B 5/107 33/2 R |

(Continued)

FOREIGN PATENT DOCUMENTS

GB    2201579 A  *  9/1988  ............... A41H 1/02

*Primary Examiner* — Christopher W Fulton (57) ABSTRACT

A bra gauging device is an apparatus which enables the wearer to measure the correct bra size corresponding to the actual bust size of the wearer, preferably up to a fraction of an inch. The apparatus includes a measurement band, a left cup-measuring mechanism, and a right cup-measuring mechanism. The measurement band facilitates the individual bust measurement of each breast as well as other breast-related measurements around the upper torso. The measurement band further supports the left cup-measuring mechanism and the right cup-measuring mechanism positioned against the breasts of the wearer. The left cup-measuring mechanism is used to measure the bust size of the left breast retained by the left cup. Likewise, the right cup-measuring mechanism is used to measure the bust size of the right breast retained by the right cup. The apparatus also includes a left wing body and a right wing body for lateral customization and support.

20 Claims, 10 Drawing Sheets

(56) References Cited

U.S. PATENT DOCUMENTS

| | | | | |
|---|---|---|---|---|
| 2,946,125 | A * | 7/1960 | Gittelson | A41H 1/02 33/2 R |
| 3,292,261 | A * | 12/1966 | Hayes | A41H 1/02 33/2 R |
| 4,219,029 | A * | 8/1980 | Grossman | A61B 5/1073 33/2 R |
| 5,414,943 | A * | 5/1995 | Vogt | A61B 5/1079 33/764 |
| 5,485,855 | A * | 1/1996 | Shiraiwa | A41H 1/02 33/511 |
| 6,272,761 | B1 * | 8/2001 | Pechter | A41H 1/02 33/17 R |
| 6,276,069 | B1 * | 8/2001 | Chadwick | G01B 3/1004 33/512 |
| 6,336,839 | B1 * | 1/2002 | Valli | A41C 3/00 450/1 |
| 6,467,180 | B1 * | 10/2002 | Chan | A41H 1/02 33/17 R |
| 9,568,296 | B2 * | 2/2017 | Moore | A41H 1/02 |
| 2013/0074353 | A1 * | 3/2013 | Petter | G01B 3/1003 33/512 |
| 2015/0342266 | A1 * | 12/2015 | Cooper | A41H 1/02 705/26.7 |
| 2015/0342278 | A1 * | 12/2015 | Butler | G01B 3/10 33/512 |
| 2016/0135513 | A1 * | 5/2016 | Solotoff | A41C 3/0021 450/52 |
| 2020/0000165 | A1 * | 1/2020 | Wang | G06T 5/003 |

* cited by examiner

BRA GAUGING DEVICE

The current application claims a priority to the U.S. Provisional Patent application Ser. No. 62/719,491 filed on Aug. 17, 2018.

FIELD OF THE INVENTION

The present invention relates generally to a measuring device. More specifically, the present invention is a measuring device to measure the exact size of each of a woman's breasts, separately, down to a fraction of an inch.

BACKGROUND OF THE INVENTION

An individual's body shape and size can differ greatly from one person to another. Ranges in body size for each person can depend on many factors such as genetics, growth irregularities, mastectomy, etc. Body shapes and sizes can widely differ especially for women. Women's breasts, specifically, greatly vary based on the shape and the position of each breast. Various traditional breast sizing systems exist; however, these traditional systems and their method of determining breast size are heavily flawed due to a lack of specific measurements pertaining to each women's breasts as these systems often measure the breasts together. Thus, irregular or unique breast sizes are often incorrectly measured.

An objective of the present invention is to address the shortcomings of old-fashioned breast measuring systems. The present invention offers a bra gauging device to measure the exact size of each breast of the wearer, separately. The present invention provides a measuring mechanism which enables the wearer to gauge the exact measurement of each breast of the wearer. The individual measurements of each of the breasts of the wearer can then be utilized to generate a custom fitting bra as well as a specific pattern for manufacturing.

DETAIL DESCRIPTIONS OF THE INVENTION

All illustrations of the drawings are for the purpose of describing selected versions of the present invention and are not intended to limit the scope of the present invention.

Figure 1:
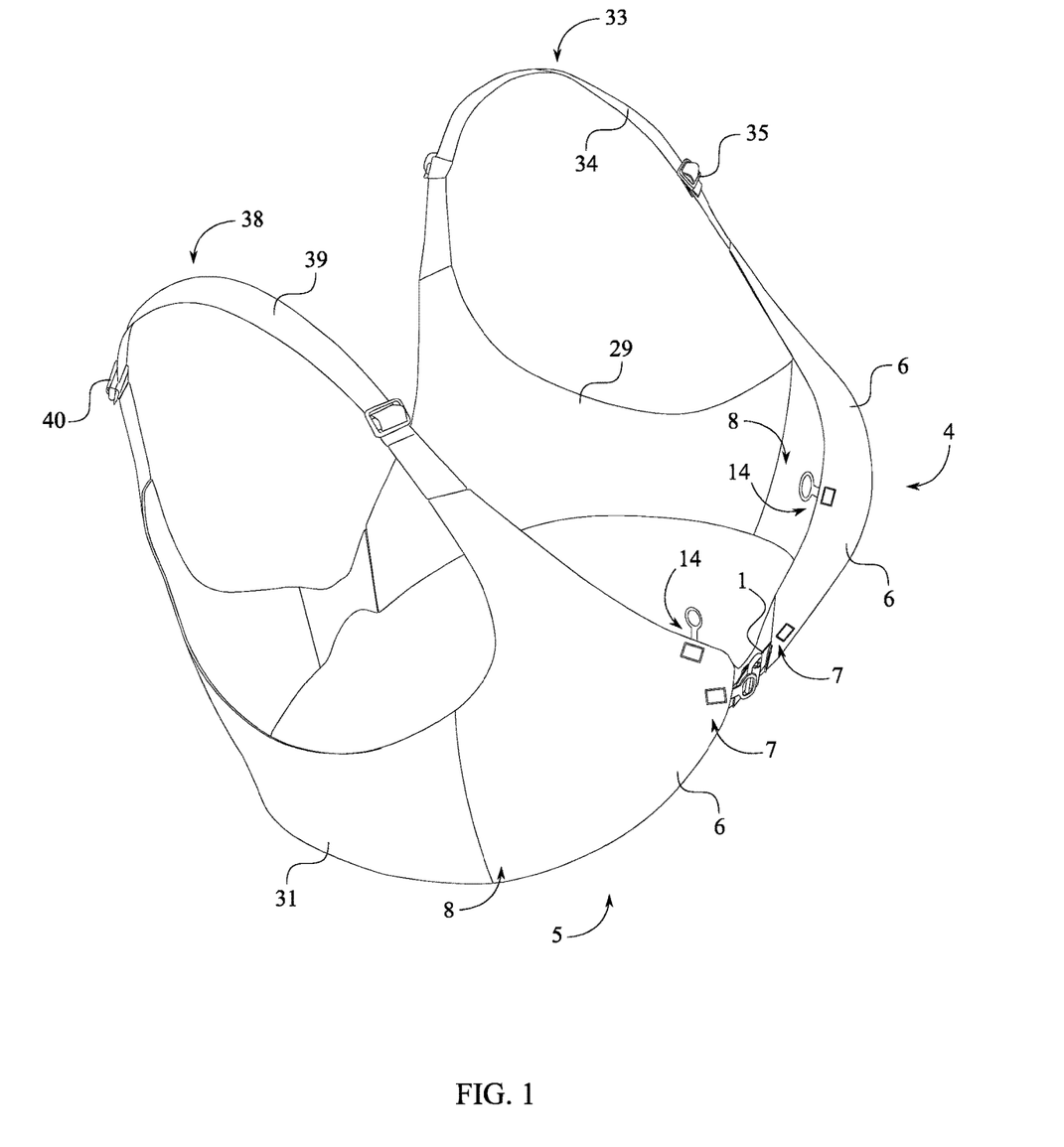
FIG. 1 is a top front perspective view of the present invention.
Figure 2:
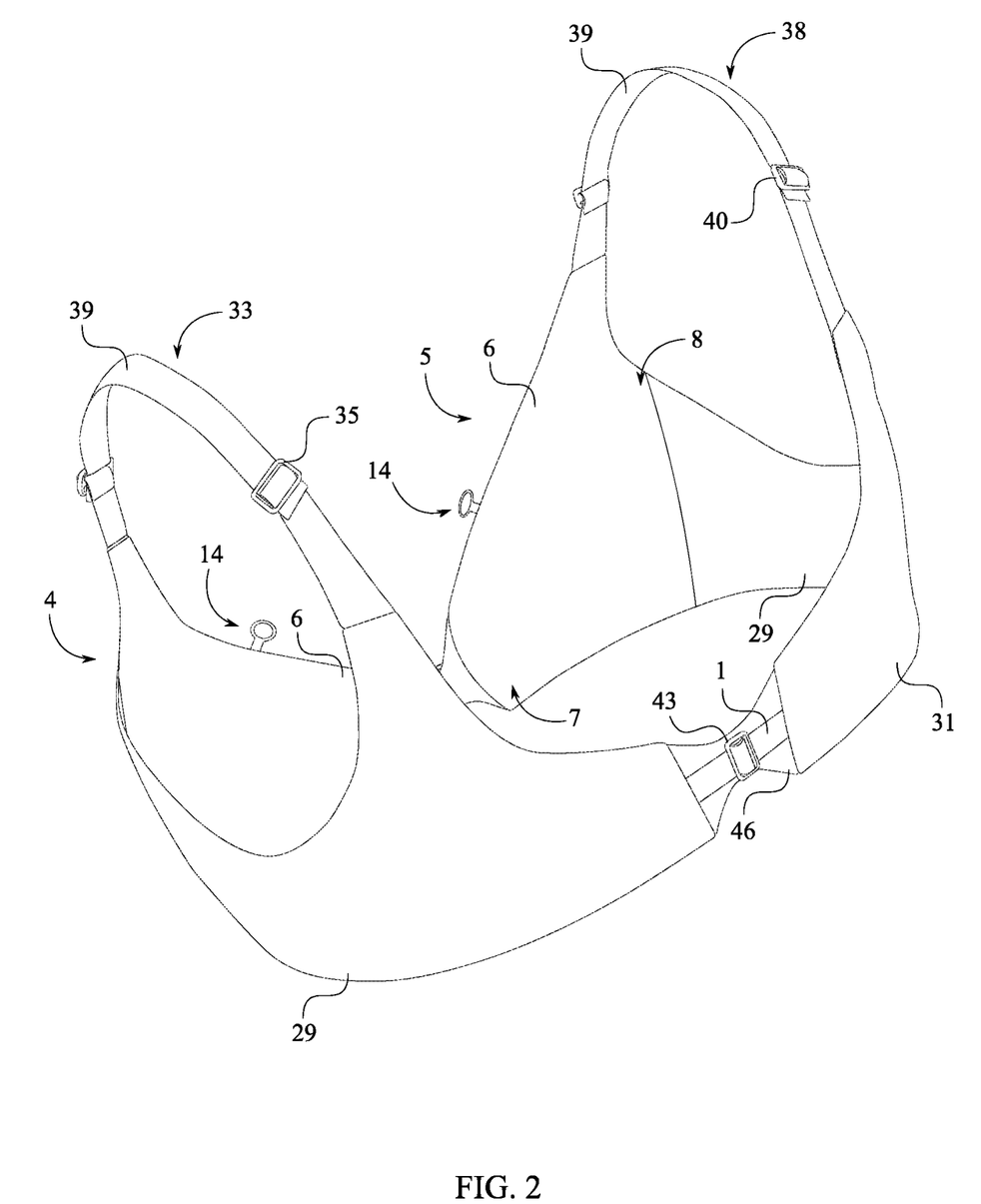
FIG. 2 is a top rear perspective view of the present invention.
Figure 3:
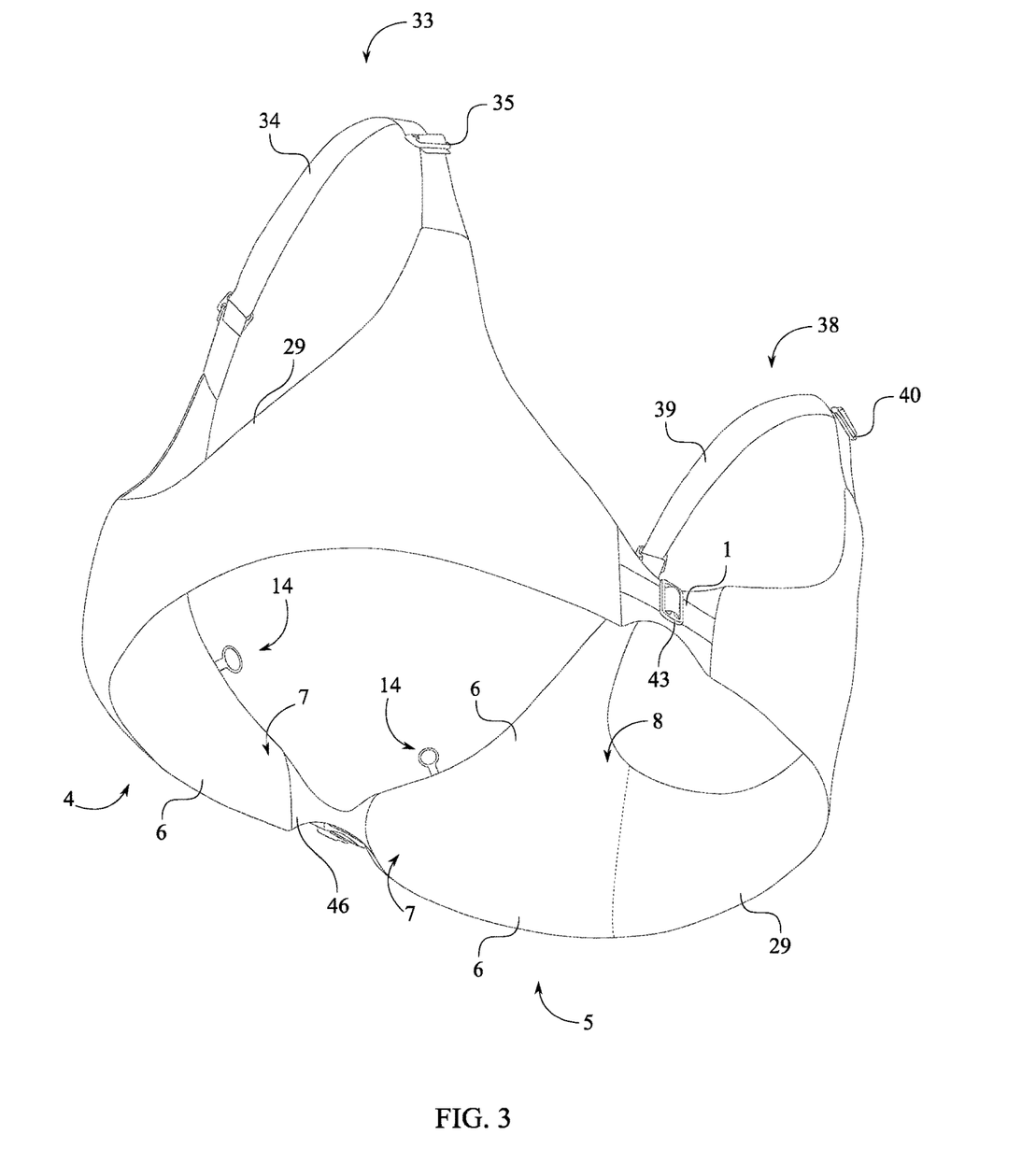
FIG. 3 is a bottom rear perspective view of the present invention.

The present invention is a bra gauging device. The present invention enables the wearer to measure the correct bra size corresponding to the actual bust size of the wearer, preferably up to a fraction of an inch. As can be seen in FIG. 1 through 3, a preferred embodiment of the present invention comprises a measurement band 1, a left cup-measuring mechanism 4, and a right cup-measuring mechanism 5. The measurement band 1 facilitates the individual bust measurement of each breast as well as other breast-related measurements around the upper torso. The measurement band 1 further supports the left cup-measuring mechanism 4 and the right cup-measuring mechanism 5 positioned against the breasts of the wearer. The left cup-measuring mechanism 4 is used to measure the bust size of the left breast retained by the left cup-measuring mechanism 4. Likewise, the right cup-measuring mechanism 5 is used to measure the bust size of the right breast retained by the right cup-measuring mechanism 5.

Figure 4:
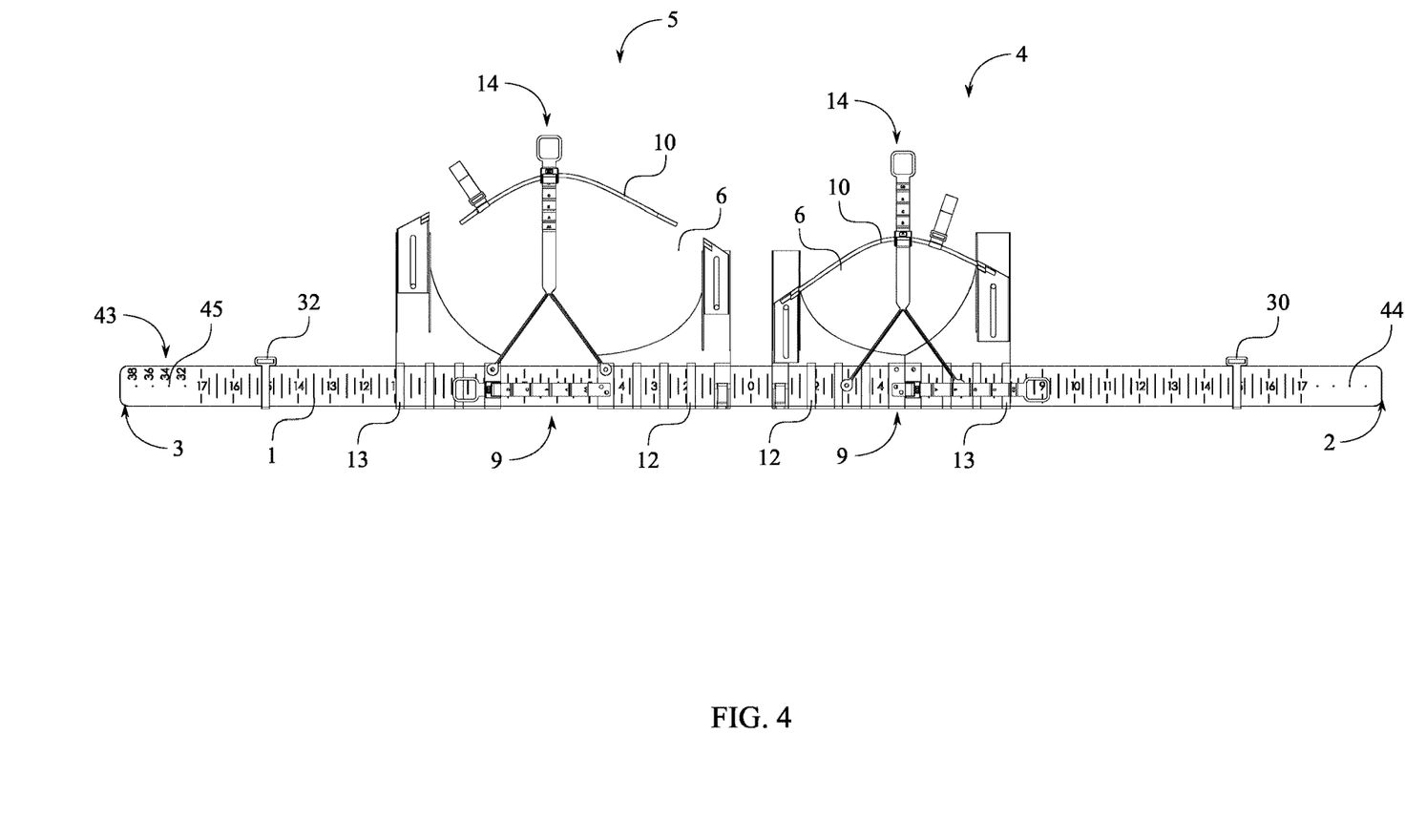
FIG. 4 is a schematic view of the measurement band, the left cup-measuring mechanism, and the right cup-measuring mechanism of the present invention.
Figure 5:
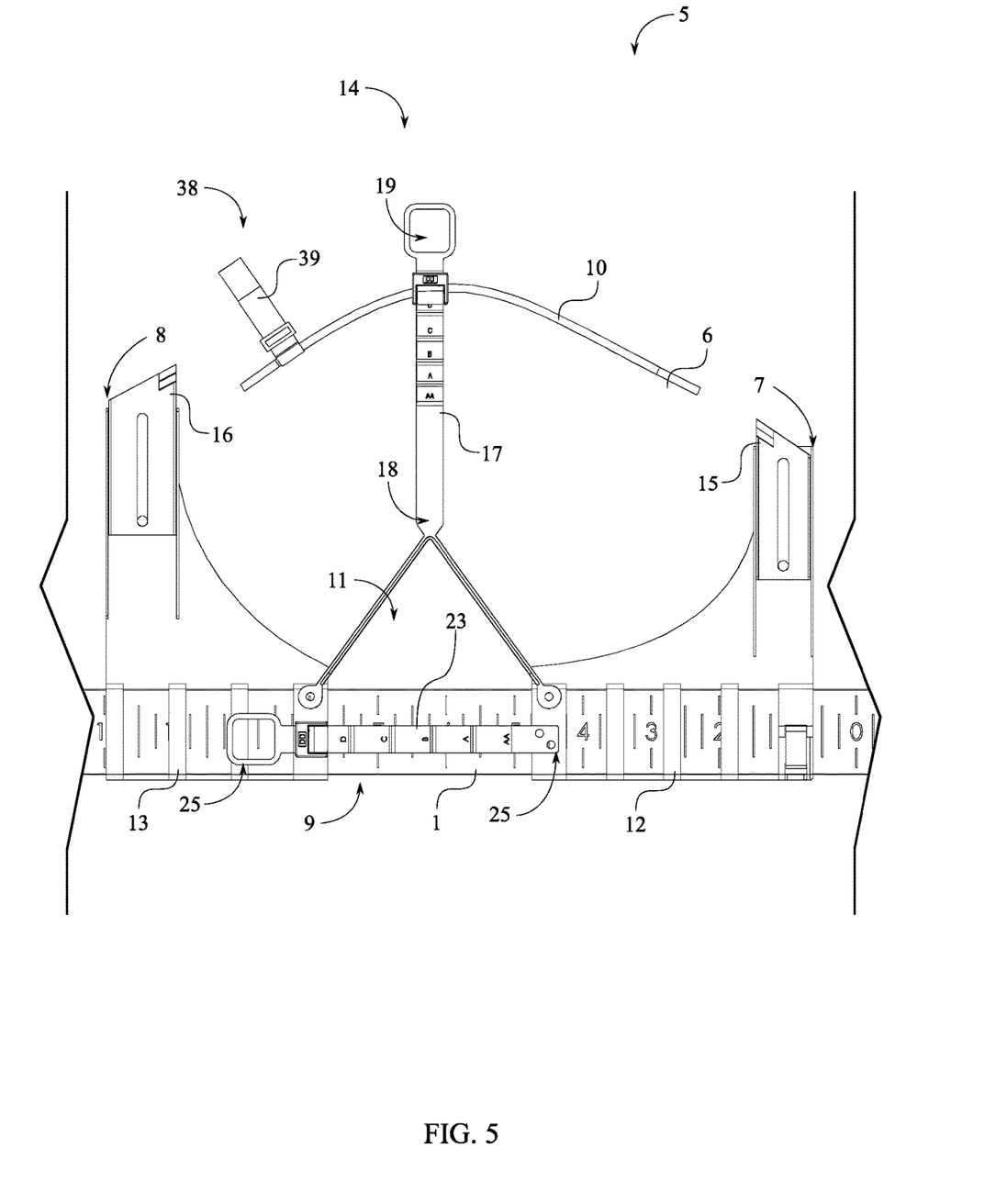
FIG. 5 is a schematic view of the right cup-measuring mechanism showing the at least one measuring tensioner in the cup body.
Figure 6:
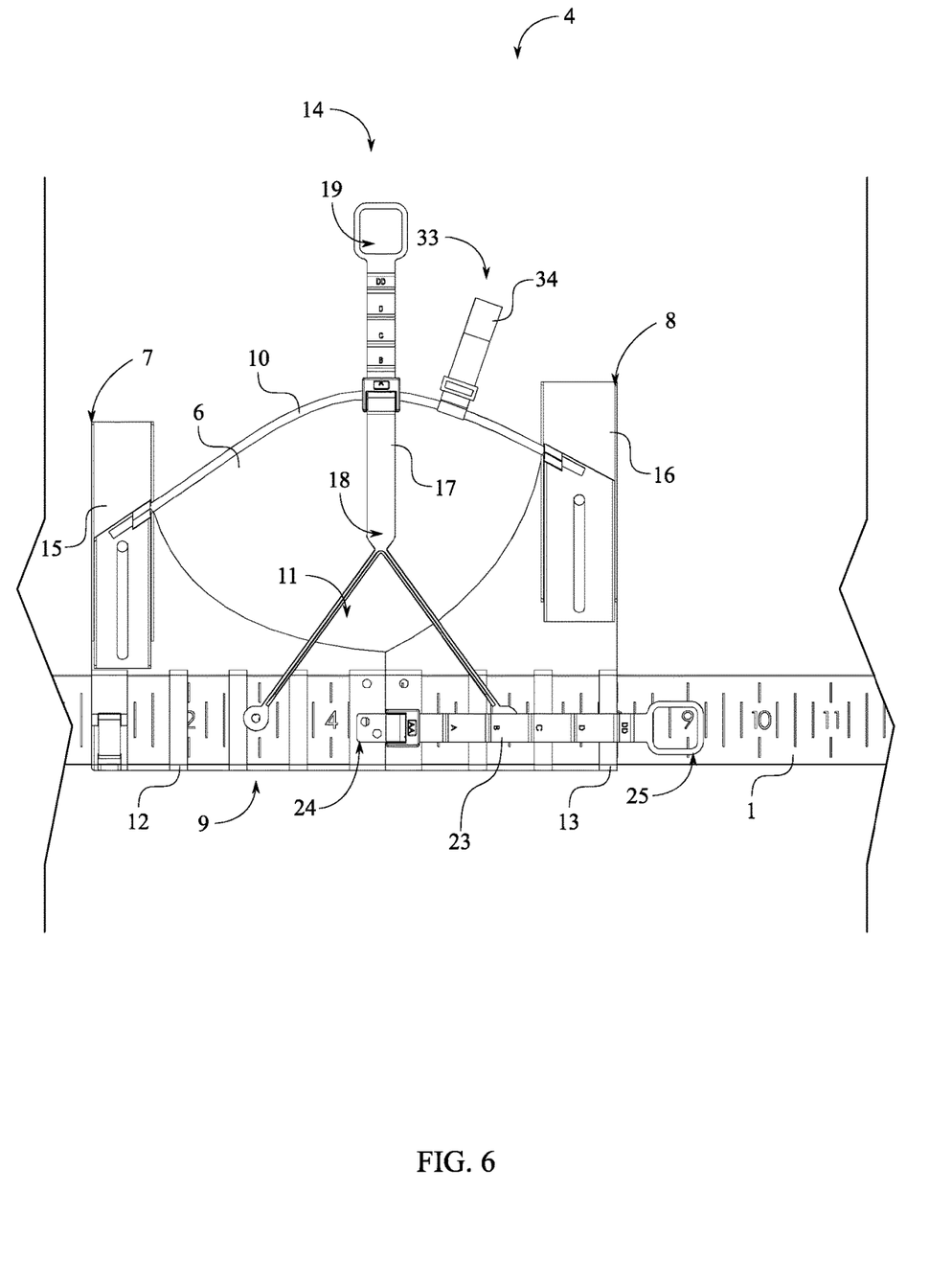
FIG. 6 is a schematic view of the left cup-measuring mechanism showing the at least one measuring tensioner in the cup body.

The general configuration of the aforementioned components allows the present invention to efficiently and effectively make measurements for a bra size which can be utilized for manufacturing of the bra. As can be seen in FIG. 1 through 4, the measurement band 1 comprises a left band end 2 and a right band end 3. The left cup-measuring mechanism 4 and the right cup-measuring mechanism 5 each comprises a cup body 6, a proximal cup clampable slider 12, and a distal cup clampable slider 13. The cup body 6 serves to retain the breast of the user. The proximal cup clampable slider 12 and the distal cup clampable slider 13 enable the sliding movement of the cup body 6 along the measurement band 1. Further, the cup body 6 comprises a proximal lateral edge 7, a distal lateral edge 8, and a base edge 9. As can be seen in FIGS. 5 and 6, the proximal lateral edge 7 and the distal lateral edge 8 are positioned opposite to each other across the cup body 6. In addition, the base edge 9 is positioned in between the proximal lateral edge 7 and the distal lateral edge 8 in order to form a perimeter of the cup body 6. The proximal lateral edge 7 is slidably connected along the measurement band 1 by the proximal cup clampable slider 12. The distal lateral edge 8 is slidably connected along the measurement band 1 by the distal cup clampable slider 13. The independent movement of the proximal cup clampable slider 12 and the distal cup clampable slider 13 allows for a dimension of the cup size to be measured along the measuring band 1. As can be seen in FIGS. 5 and 6, the distal cup clampable slider 13 and the proximal cup clampable slider 12 are positioned adjacent to the base edge 9 to facilitate the sliding of the cup body 6 along the measurement band 1. The distal cup clampable slider 13 and the proximal cup clampable slider 12 is preferably a ratcheting mechanism which enables the sliding movement of the distal cup clampable slider 13 and the proximal cup clampable slider 12. Also, the ratcheting mechanism locks the distal cup clampable slider 13 and the proximal cup clampable slider 12 at the desired position along the measurement band 1. The distal lateral edge 8 of the left cup-measuring mechanism 4 is positioned in between the proximal lateral edge 7 of the left cup-measuring mechanism 4 and the left band end 2. On the other hand, the distal lateral edge 8 of the right cup-measuring mechanism 5 is positioned in between the proximal lateral edge 7 of the right cup-measuring mechanism 5 and the right band end 3. Thus, the left cup-measuring mechanism 4 and the right cup-measuring mechanism 5 are provided offset from each other along the measurement band 1. As can be seen in FIG. 4, the space in between the left cup-measuring mechanism 4 and the right cup-measuring mechanism 5 preferably corresponds to the bridge of a bra.

The left cup-measuring mechanism 4 and the right cup-measuring mechanism 5 each enables the individual measurement of each breast size. As can be seen in FIGS. 5 and 6, the left cup-measuring mechanism 4 and the right cup-measuring mechanism 5 each further comprises at least one measuring tensioner 14. The at least one measuring tensioner 14 allows for size measurements of various sections of the cup body 6. The at least one measuring tensioner 14 is operatively integrated into the cup body 6, wherein the at least one measuring tensioner 14 is used to measure a bust size of a breast retained by the cup body 6. In alternate embodiments, the at least one measuring tensioner 14 is a plurality of measuring tensioners distributed about the cup body 6 to measure various sections of the cup body 6.

To enable the correct measurement of the breast size, the at least one measuring tensioner 14 can be adjusted to match the actual size of the breast. As can be seen in FIGS. 5 and 6, the at least one measuring tensioner 14 comprises a proximal lateral clampable slider 15 and a distal lateral clampable slider 16. The proximal lateral clampable slider 15 is connected onto the proximal cup clampable slider 12 so the proximal lateral clampable slider 15 slides along the measurement band 1 along with the proximal cup clampable slider 12. In addition, the proximal lateral edge 7 is slidably connected along the proximal lateral clampable slider 15 so proximal lateral edge 7 is extended or contracted according to the movement of the proximal lateral clampable slider 15. Likewise, the distal lateral clampable slider 16 is connected onto the distal cup clampable slider 13 so the distal lateral clampable slider 16 slides along the measurement band 1 along with the distal lateral clampable slider 16. The distal lateral edge 8 is also slidably connected along the distal lateral clampable slider 16 like the proximal lateral edge 7. Thus, the distal lateral clampable slider 16 is able to move in perpendicular directions with the distal lateral clampable slider 16 along with the distal lateral edge 8. As can be seen in FIGS. 5 and 6, the proximal lateral clampable slider 15 and a distal lateral clampable slider 16 is preferably a sliding mechanism which ensures the sliding movement of the proximal lateral clampable slider 15 and a distal lateral clampable slider 16.

Figure 7:
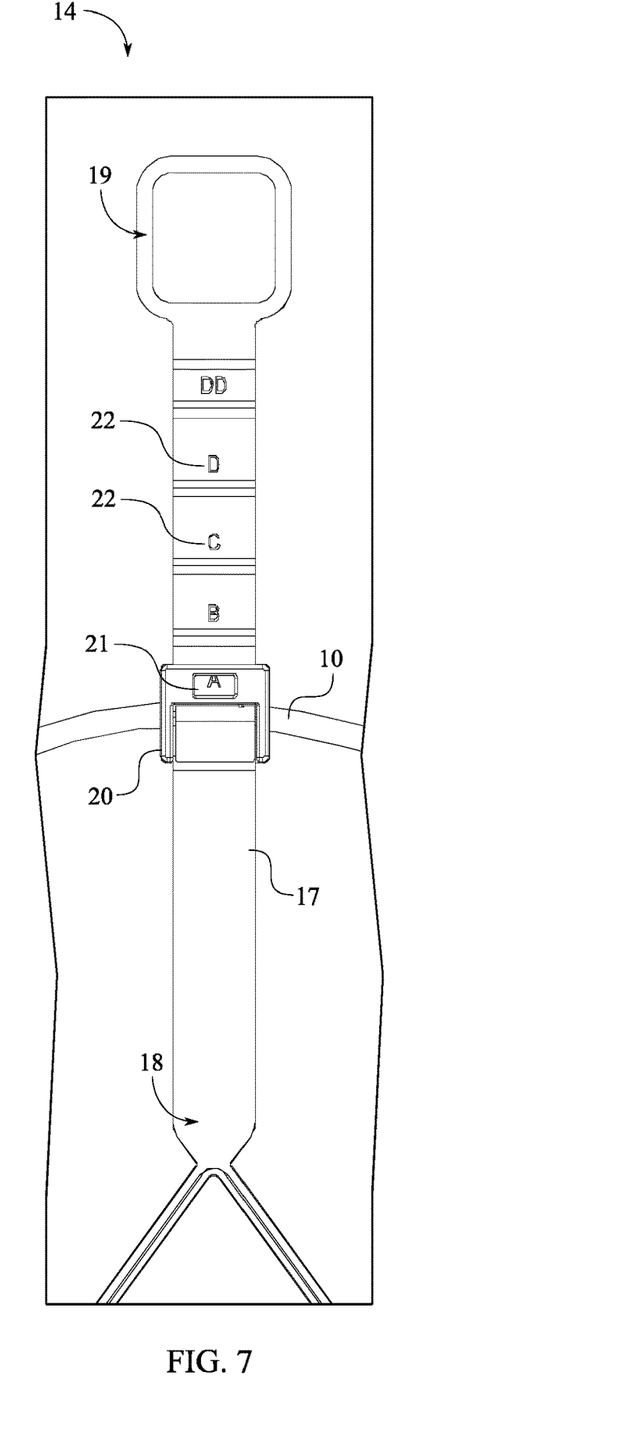
FIG. 7 is a schematic view of the first pull tab of the at least one measuring tensioner.

As can be seen in FIG. 7, the at least one measuring tensioner 14 enables vertical measurement of the cup body 6 for more accurate measurement of the breast size. The cup body 6 further comprises a top edge 10 to form a closed structure. As can be seen in FIG. 7, the at least one measuring tensioner 14 comprises a first pull tab 17, a first clampable sleeve 20, a first window 21, and a first set of markers 22. In addition, the first pull tab 17 comprises a first fixed tab end 18 and a first free tab end 19. As can be seen in FIGS. 5 and 6, the top edge 10 and the base edge 9 are positioned opposite to each other across the cup body 6 to close the perimeter of the cup body 6. The first fixed tab end 18 is tethered to the proximal cup clampable slider 12. The first fixed tab end 18 is also tethered to the distal cup clampable slider 13. Thus, the vertical movement of the first pull tab 17 results in the sliding of the proximal cup clampable slider 12 as well as the sliding of the distal cup clampable slider 13 along the measurement band 1. Further, the first clampable sleeve 20 is integrated into the top edge 10 to receive the first pull tab 17. As can be seen in FIG. 7, the first pull tab 17 is slidably positioned through the first clampable sleeve 20 to enable vertical movement of the first pull tab 17 through the first clampable sleeve 20. The first clampable sleeve 20 is preferably a ratcheting mechanism which enables the sliding movement of the first pull tab 17. Also, the ratcheting mechanism locks the first pull tab 17 at the desired length which adjusts the cup body 6 to the actual bust size. The first clampable sleeve 20 is also positioned in between the first fixed tab end 18 and the first free tab end 19 so the first free tab end 19 is easily graspable, offset from the cup body 6. Furthermore, the first set of markers 22 is inscribed along the first pull tab 17 to facilitate the vertical measurement of the cup body 6. In addition, the first window 21 is integrated into the first clampable sleeve 20 to help determine the vertical size measurement of the cup body 6 by allowing the user to view the first set of markers 22 through the first window 21. In some embodiments of the present invention, the first set of markers 22 may comprise a color-coded pattern to facilitate the vertical measurement of the cup body 6.

To enable adjustment of the cup body 6, the cup body 6 comprises flexibility capabilities to facilitate the sliding of the various components. As can be seen in FIGS. 5 and 6, the cup body 6 further comprises an expandable portion 11. The expandable portion 11 is positioned along the base edge 9 to facilitate expansion or contraction of the cup body 6 in all directions. The expandable portion 11 is also positioned adjacent to the distal cup clampable slider 13 and the proximal cup clampable slider 12 to not obstruct the movement of the distal cup clampable slider 13 and the proximal cup clampable slider 12. In alternate embodiments, the expandable portion 11 can be distributed about the whole cup body 6.

Figure 8:
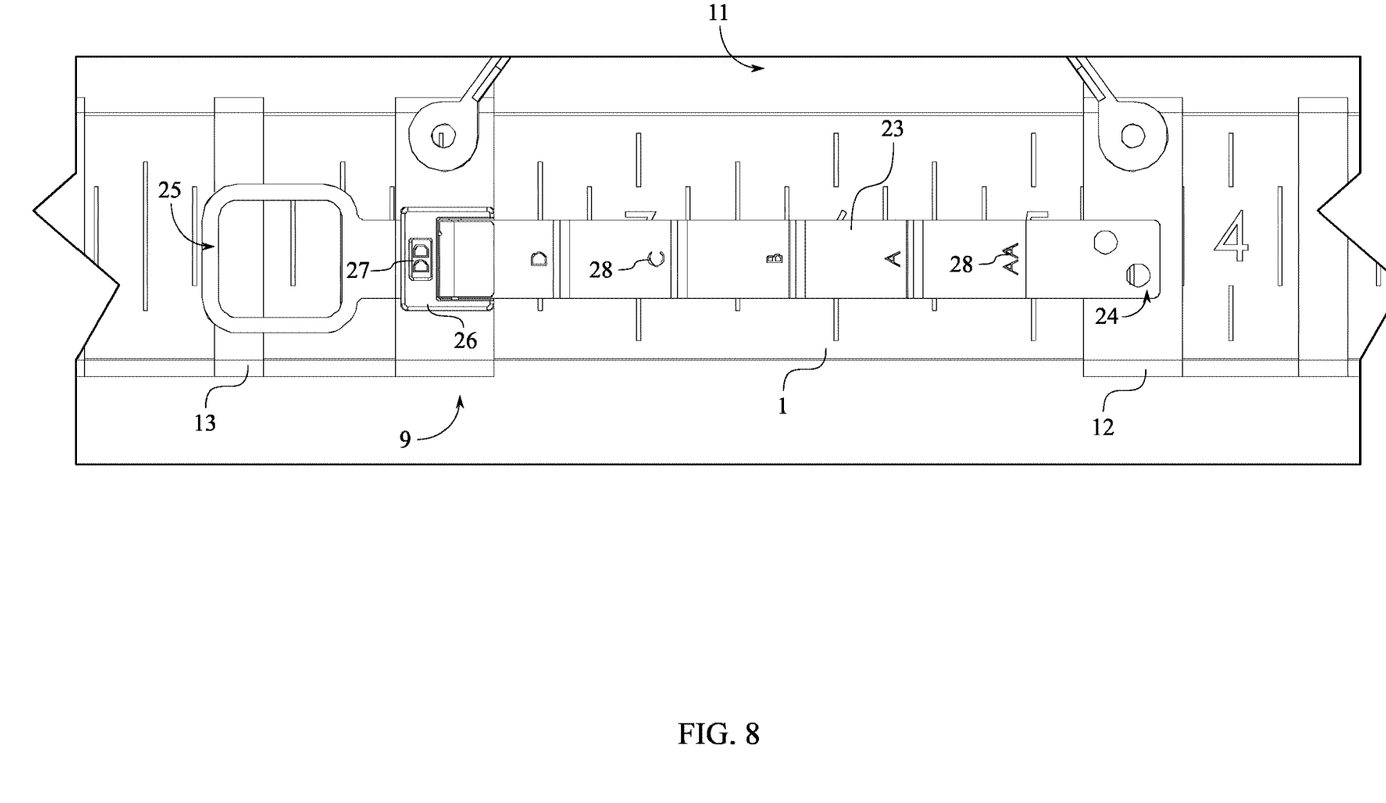
FIG. 8 is a schematic view of the second pull tab of the at least one measuring tensioner.

The at least one measuring tensioner 14 further provides means for horizontal measurement of the cup body 6. As can be seen in FIG. 8, the at least one measuring tensioner 14 comprises a second pull tab 23, a second clampable sleeve 26, a second window 27, and a second set of markers 28. Like the first pull tab 17, the second pull tab 23 comprises a second fixed tab end 24 and a second free tab end 25. However, the second fixed tab end 24 is connected onto the proximal cup clampable slider 12 to move the proximal cup clampable slider 12 when the second pull tab 23 is moved. As can be seen in FIG. 8, the second clampable sleeve 26 is connected onto the distal cup clampable slider 13 to receive the second pull tab 23. The second clampable sleeve 26 is also positioned in between the second fixed tab end 24 and the second free tab end 25 so the second free tab end 25 is positioned externally to the cup body 6. The second pull tab 23 is slidably positioned through the second clampable sleeve 26. The second clampable sleeve 26 is preferably a ratcheting mechanism like the first clampable sleeve 20 which enables the sliding movement of the second pull tab 23. Also, the ratcheting mechanism locks the second pull tab 23 at the desired length which adjusts the cup body 6 size to the actual bust size. In addition, the second set of markers 28 is inscribed along the second pull tab 23 to facilitate the horizontal measurement of the cup body 6. Finally, the second window 27 is integrated into the second clampable sleeve 26 to help determine the horizontal size measurement of the cup body 6 by allowing the user to view the second set of markers 28 through the second window 27. In some embodiments of the present invention, the second set of markers 28 may comprise a color-coded pattern to facilitate the measurement of the cup body 6.

The present invention further provides lateral support which can be measured for additional customization. As can be seen in FIG. 1 through 4, the present invention further comprises a left wing body 29 and a left wing clampable slider 30. The left wing clampable slider 30 is positioned in between the left band end 2 and the distal lateral edge 8 of the left cup-measuring mechanism 4 so the left wing clampable slider 30 is provided offset the left band end 2. The left wing clampable slider 30 is preferably a ratcheting mechanism like the second clampable sleeve 26. Also, the ratcheting mechanism locks the left wing clampable slider 30 at the desired length which adjusts the left wing body 29 to the desired wing size. The left wing clampable slider 30 is also slidably connected along the measurement band 1 to facilitate the measurement of size of the left wing body 29. In addition, the left wing body 29 is connected in between the left wing clampable slider 30 and the distal lateral edge 8 of the left cup-measuring mechanism 4 to enable the measurement of the left wing body 29.

Opposite the left wing body 29 and the left wing clampable slider 30, the present invention further comprises a right wing body 31 and a right wing clampable slider 32. As can be seen in FIG. 1 through 4, the right wing clampable slider 32 is positioned in between the right band end 3 and the distal lateral edge 8 of the right cup-measuring mechanism 5 so the right wing body 31 is provided offset the right band end 3. The right wing clampable slider 32 is also slidably connected along the measurement band 1 to facilitate adjustments of the right wing body 31. The right wing body 31 is connected in between the right wing clampable slider 32 and the distal lateral edge 8 of the right cup-measuring mechanism 5. Thus, the right wing clampable slider 32 can be slid along the measurement band 1 to measure the size of the right wing body 31.

Figure 9:
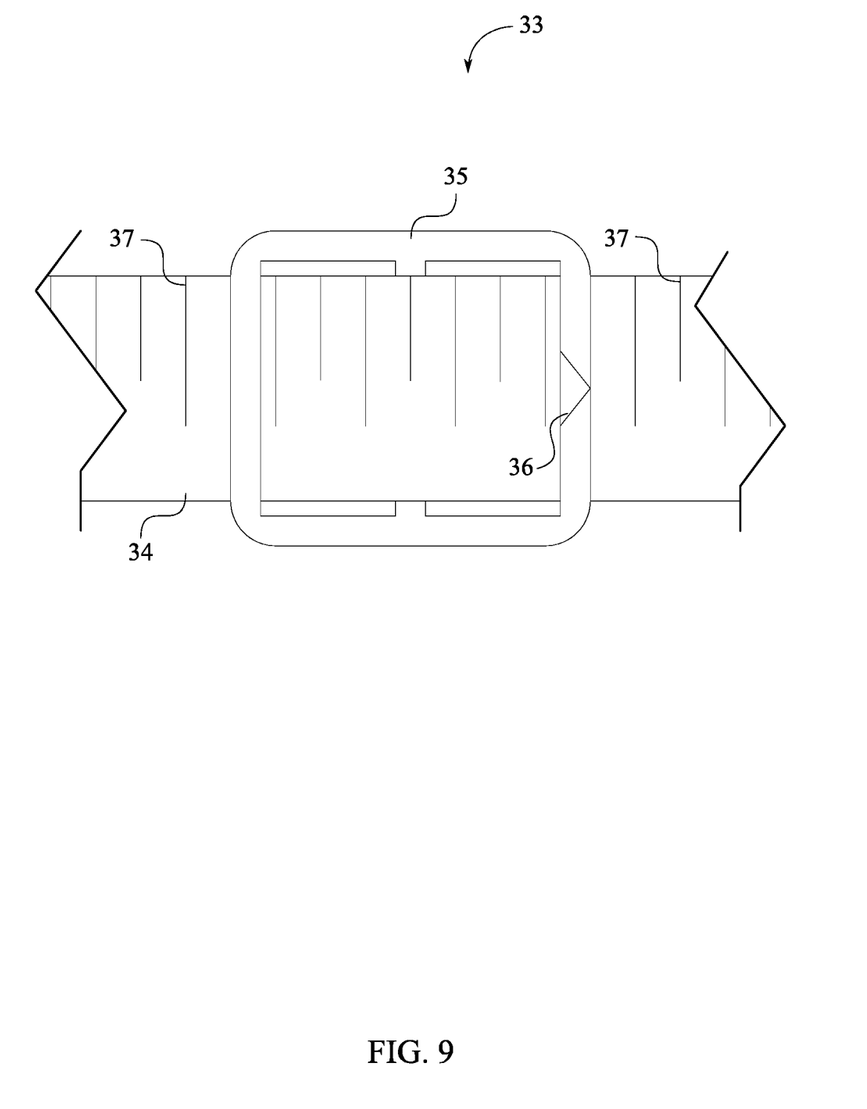
FIG. 9 is a schematic view of the left shoulder measuring strap.

To provide vertical support, the present invention further comprises a left shoulder measuring strap 33. The left shoulder measuring strap 33 is connected in between the left wing clampable slider 30 and the top edge 10 of the left cup-measuring mechanism 4 so the left shoulder measuring strap 33 rests on the left shoulder of the user. Furthermore, the left shoulder measuring strap 33 is further able to be adjusted to obtain measurements. As can be seen in FIG. 9, the left shoulder measuring strap 33 comprises a left strap body 34, at least one left loop-forming strap buckle 35, at least one left strap indicator 36, and a plurality of left strap markers 37. The at least one left loop-forming strap buckle 35 is slidably engaged along the left strap body 34 to facilitate the working length adjustment of the left shoulder measuring strap 33. The at least one left strap indicator 36 is integrated into the at least one left loop-forming strap buckle 35. In addition, the plurality of left strap markers 37 is inscribed along the left strap body 34 so the user can determine the working length of the left shoulder measuring strap 33. The at least one left strap indicator 36 helps determine the marker of the plurality of left strap markers 37 corresponding to working length of the left shoulder measuring strap 33. Further, the at least one left loop-forming strap buckle 35 is preferably a similar ratcheting mechanism provided on the first clampable sleeve 20 and second clampable sleeve 26. In some embodiments of the present invention, the plurality of left strap markers 37 may comprise a color-coded pattern to facilitate the measurement of the left strap body 34.

Figure 10:
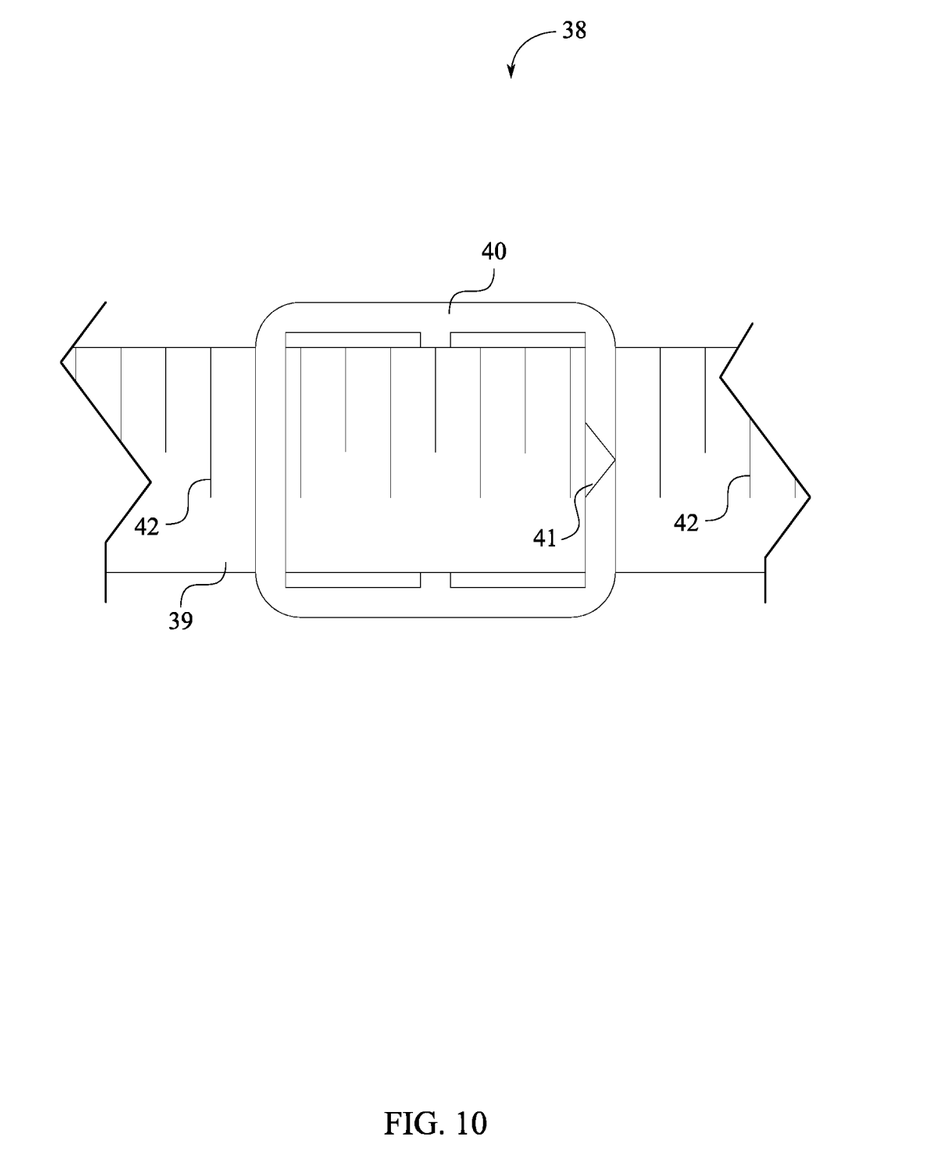
FIG. 10 is a schematic view of the right shoulder measuring strap.

As can be seen in FIG. 1 through 4, opposite the left shoulder measuring strap 33, the present invention further comprises a right shoulder measuring strap 38 to balance the weight of the breasts on the shoulders of the user. Further, the right shoulder measuring strap 38 is connected in between the right wing clampable slider 32 and the top edge 10 of the right cup-measuring mechanism 5 so the right shoulder measuring strap 38 rests on the right shoulder of the user. Like the left shoulder measuring strap 33, the right shoulder measuring strap 38 is further able to be adjusted to obtain measurements. As can be seen in FIG. 10, the right shoulder measuring strap 38 comprises a right strap body 39, at least one right loop-forming strap buckle 40, at least one right strap indicator 41, and a plurality of right strap markers 42. The at least one right loop-forming strap buckle 40 is slidably engaged along the right strap body 39 to facilitate the working length adjustment of the right shoulder measuring strap 38. Further, the at least one right loop-forming strap buckle 40 is preferably a similar ratcheting mechanism to the at least one left loop-forming strap buckle 35. The at least one right strap indicator 41 is integrated into the at least one right loop-forming strap buckle 40. In addition, the plurality of right strap markers 42 is inscribed along the right strap body 39 so the user can determine the working length of the right shoulder measuring strap 38. The at least one left strap indicator 41 helps determine the marker of the plurality of left strap markers 42 corresponding to working length of the left shoulder measuring strap 38. In some embodiments of the present invention, the plurality of right strap markers 42 may comprise a color-coded pattern to facilitate the measurement of the right strap body 39.

To secure the measurement band 1 around the upper torso, the present invention further comprises a length-adjustable fastener 43. As can be seen in FIG. 4, the length-adjustable fastener 43 comprises a left interlocking piece 44 and a right interlocking piece 45. The left interlocking piece 44 and the right interlocking piece 45 are preferably locking devices with matching structures which can be selectively engaged or disengaged to fasten the left band end 2 to the right band end 3. The left interlocking piece 44 is connected along the measurement band 1, adjacent to the left band end 2. In addition, the right interlocking piece 45 is connected along the measurement band 1, adjacent to the right band end 3. Thus, the measurement band 1 can be secured by fastening the left interlocking piece 44 to the right interlocking piece 45. The working length of the measurement band 1 can also be adjusted by repositioning the left interlocking piece 44 and the right interlocking piece 45 at different positions along the measurement band 1.

In some embodiments, the present invention comprises a bra body 46 to protect the skin of the user. As can be seen in FIG. 1 through 3, the cup body 6 of the left cup-measuring mechanism 4 and the cup body 6 of the right cup-measuring mechanism 5 are integrated into the bra body 46 to protect the breasts of the user. The bra body 46 is further made of an expandable fabric to facilitate the length adjustments of the present invention.

Although the invention has been explained in relation to its preferred embodiment, it is to be understood that many other possible modifications and variations can be made without departing from the spirit and scope of the invention as hereinafter claimed.

What is claimed is:

1. A bra gauging device comprises:
   a measurement band;
   a left cup-measuring mechanism;
   a right cup-measuring mechanism;
   the measurement band comprising a left band end and a right band end;
   the left cup-measuring mechanism and the right cup-measuring mechanism each comprising the cup body, a proximal cup clampable slider, and a distal cup clampable slider;
   the cup body comprising a proximal lateral edge, a distal lateral edge, and a base edge;
   the proximal lateral edge and the distal lateral edge being positioned opposite to each other across the cup body;

the base edge being positioned in between the proximal lateral edge and the distal lateral edge;

the proximal lateral edge being slidably connected along the measurement band by the proximal cup clampable slider;

the distal lateral edge being slidably connected along the measurement band by the distal cup clampable slider;

the distal cup clampable slider and the proximal cup clampable slider being positioned adjacent to the base edge;

the distal lateral edge of the left cup-measuring mechanism being positioned in between the proximal lateral edge of the left cup-measuring mechanism and the left band end; and, the distal lateral edge of the right cup-measuring mechanism being positioned in between the proximal lateral edge of the right cup-measuring mechanism and the right band end.

2. The bra gauging device as claimed as claim 1 comprises:

the left cup-measuring mechanism and the right cup-measuring mechanism each further comprising at least one measuring tensioner; and, the at least one measuring tensioner being operatively integrated into the cup body, wherein the at least one measuring tensioner is used to measure a bust size of a breast retained by the cup body.

3. The bra gauging device as claimed as claim 2 comprises:

the at least one measuring tensioner comprising a proximal lateral clampable slider and a distal lateral clampable slider;

the proximal lateral clampable slider being connected onto the proximal cup clampable slider;

the proximal lateral edge being slidably connected along the proximal lateral clampable slider;

the distal lateral clampable slider being connected onto the distal cup clampable slider; and, the distal lateral edge being slidably connected along the distal lateral clampable slider.

4. The bra gauging device as claimed as claim 2 comprises:

the cup body further comprising a top edge;

the at least one measuring tensioner comprising a first pull tab, a first clampable sleeve, a first window, and a first set of markers;

the first pull tab comprising a first fixed tab end and a first free tab end;

the top edge and the base edge being positioned opposite to each other across the cup body;

the first fixed tab end being tethered to the proximal cup clampable slider;

the first fixed tab end being tethered to the distal cup clampable slider;

the first clampable sleeve being integrated into the top edge;

the first pull tab being slidably positioned through the first clampable sleeve;

the first clampable sleeve being positioned in between the first fixed tab end and the first free tab end;

the first set of markers being inscribed along the first pull tab; and, the first window being integrated into the first clampable sleeve.

5. The bra gauging device as claimed as claim 2 comprises:

the cup body further comprising an expandable portion;

the expandable portion being positioned along the base edge; and, the expandable portion being positioned adjacent to the distal cup clampable slider and the proximal cup clampable slider.

6. The bra gauging device as claimed as claim 2 comprises:

the at least one measuring tensioner comprising a second pull tab, a second clampable sleeve, a second window, and a second set of markers;

the second pull tab comprising a second fixed tab end and a second free tab end;

the second fixed tab end being connected onto the proximal cup clampable slider;

the second clampable sleeve being connected onto the distal cup clampable slider;

the second clampable sleeve being positioned in between the second fixed tab end and the second free tab end;

the second pull tab being slidably positioned through the second clampable sleeve;

the second set of markers being inscribed along the second pull tab; and, the second window being integrated into the second clampable sleeve.

7. The bra gauging device as claimed as claim 1 comprises:

a left wing body;

a left wing clampable slider;

the left wing clampable slider being positioned in between the left band end and the distal lateral edge of the left cup-measuring mechanism;

the left wing clampable slider being slidably connected along the measurement band; and, the left wing body being connected in between the left wing clampable slider and the distal lateral edge of the left cup-measuring mechanism.

8. The bra gauging device as claimed as claim 1 comprises:

a right wing body;

a right wing clampable slider;

the right wing clampable slider being positioned in between the right band end and the distal lateral edge of the right cup-measuring mechanism;

the right wing clampable slider being slidably connected along the measurement band; and, the right wing body being connected in between the right wing clampable slider and the distal lateral edge of the right cup-measuring mechanism.

9. The bra gauging device as claimed in claim 1 further comprises:

a left shoulder measuring strap;

a left wing clampable slider;

the cup body further comprising a top edge;

the top edge and the base edge being positioned opposite to each other across the cup body;

the left wing clampable slider being positioned in between the left band end and the distal lateral edge of the left cup-measuring mechanism;

the left wing clampable slider being slidably connected along the measurement band; and, the left shoulder measuring strap being connected in between the left wing clampable slider and the top edge of the left cup-measuring mechanism.

10. The bra gauging device as claimed in claim 9 further comprises:

the left shoulder measuring strap comprising a left strap body, at least one left loop-forming strap buckle, at least one left strap indicator, and a plurality of left strap markers;
the at least one left loop-forming strap buckle being slidably engaged along the left strap body;
the at least one left strap indicator being integrated into the at least one left loop-forming strap buckle; and,
the plurality of left strap markers being inscribed along the left strap body.

11. The bra gauging device as claimed in claim 1 further comprises:
a right shoulder measuring strap;
a right wing clampable slider;
the cup body further comprising a top edge;
the top edge and the base edge being positioned opposite to each other across the cup body;
the right wing clampable slider being positioned in between the right band end and the distal lateral edge of the right cup-measuring mechanism;
the right wing clampable slider being slidably connected along the measurement band; and,
the right shoulder measuring strap being connected in between the right wing clampable slider and the top edge of the right cup-measuring mechanism.

12. The bra gauging device as claimed in claim 11 further comprises:
the right shoulder measuring strap comprising a right strap body, at least one right loop-forming strap buckle, at least one right strap indicator, and a plurality of right strap markers;
the at least one right loop-forming strap buckle being slidably engaged along the right strap body;
the at least one right strap indicator being integrated into the at least one right loop-forming strap buckle; and,
the plurality of right strap markers being inscribed along the right strap body.

13. The bra gauging device as claimed in claim 1 further comprises:
a length-adjustable fastener;
the length-adjustable fastener comprising a left interlocking piece and a right interlocking piece;
the left interlocking piece being connected along the measuring band, adjacent to the left band end; and,
the right interlocking piece being connected along the measuring band, adjacent to the right band end.

14. The bra gauging device as claimed in claim 1 further comprises:
a bra body;
the cup body of the left cup-measuring mechanism and the cup body of the right cup-measuring mechanism being integrated into the bra body; and,
the bra body being made of an expandable fabric.

15. A bra gauging device comprises:
a measurement band;
a left cup-measuring mechanism;
a right cup-measuring mechanism;
a bra body;
a length-adjustable fastener;
the length-adjustable fastener comprising a left interlocking piece and a right interlocking piece;
the measurement band comprising a left band end and a right band end;
the left cup-measuring mechanism and the right cup-measuring mechanism each comprising the cup body, a proximal cup clampable slider, and a distal cup clampable slider;
the cup body comprising a proximal lateral edge, a distal lateral edge, and a base edge;
the proximal lateral edge and the distal lateral edge being positioned opposite to each other across the cup body;
the base edge being positioned in between the proximal lateral edge and the distal lateral edge;
the proximal lateral edge being slidably connected along the measurement band by the proximal cup clampable slider;
the distal lateral edge being slidably connected along the measurement band by the distal cup clampable slider;
the distal cup clampable slider and the proximal cup clampable slider being positioned adjacent to the base edge;
the distal lateral edge of the left cup-measuring mechanism being positioned in between the proximal lateral edge of the left cup-measuring mechanism and the left band end;
the distal lateral edge of the right cup-measuring mechanism being positioned in between the proximal lateral edge of the right cup-measuring mechanism and the right band end;
the cup body of the left cup-measuring mechanism and the cup body of the right cup-measuring mechanism being integrated into the bra body;
the bra body being made of an expandable fabric;
the left interlocking piece being connected along the measuring band, adjacent to the left band end; and,
the right interlocking piece being connected along the measuring band, adjacent to the right band end.

16. The bra gauging device as claimed as claim 15 comprises:
the left cup-measuring mechanism and the right cup-measuring mechanism each further comprising at least one measuring tensioner;
the cup body further comprising an expandable portion;
the at least one measuring tensioner being operatively integrated into the cup body, wherein the at least one measuring tensioner is used to measure a bust size of a breast retained by the cup body;
the expandable portion being positioned along the base edge; and,
the expandable portion being positioned adjacent to the distal cup clampable slider and the proximal cup clampable slider.

17. The bra gauging device as claimed as claim 16 comprises:
the cup body further comprising a top edge;
the at least one measuring tensioner comprising a proximal lateral clampable slider, a distal lateral clampable slider, a first pull tab, a first clampable sleeve, a first window, a first set of markers, a second pull tab, a second clampable sleeve, a second window, and a second set of markers;
the proximal lateral clampable slider being connected onto the proximal cup clampable slider;
the proximal lateral edge being slidably connected along the proximal lateral clampable slider;
the distal lateral clampable slider being connected onto the distal cup clampable slider;
the distal lateral edge being slidably connected along the distal lateral clampable slider;
the first pull tab comprising a first fixed tab end and a first free tab end;
the top edge and the base edge being positioned opposite to each other across the cup body;

the first fixed tab end being tethered to the proximal cup clampable slider;
the first fixed tab end being tethered to the distal cup clampable slider;
the first clampable sleeve being integrated into the top edge;
the first pull tab being slidably positioned through the first clampable sleeve;
the first clampable sleeve being positioned in between the first fixed tab end and the first free tab end;
the first set of markers being inscribed along the first pull tab;
the first window being integrated into the first clampable sleeve;
the second pull tab comprising a second fixed tab end and a second free tab end;
the second fixed tab end being connected onto the proximal cup clampable slider;
the second clampable sleeve being connected onto the distal cup clampable slider;
the second clampable sleeve being positioned in between the second fixed tab end and the second free tab end;
the second pull tab being slidably positioned through the second clampable sleeve;
the second set of markers being inscribed along the second pull tab; and,
the second window being integrated into the second clampable sleeve.

18. The bra gauging device as claimed as claim 15 comprises:
a left wing body;
a left wing clampable slider;
a right wing body;
a right wing clampable slider;
the left wing clampable slider being positioned in between the left band end and the distal lateral edge of the left cup-measuring mechanism;
the left wing clampable slider being slidably connected along the measurement band;
the left wing body being connected in between the left wing clampable slider and the distal lateral edge of the left cup-measuring mechanism;
the right wing clampable slider being positioned in between the right band end and the distal lateral edge of the right cup-measuring mechanism;
the right wing clampable slider being slidably connected along the measurement band; and,
the right wing body being connected in between the right wing clampable slider and the distal lateral edge of the right cup-measuring mechanism.

19. The bra gauging device as claimed in claim 15 further comprises:
a left shoulder measuring strap;
a left wing clampable slider;
the cup body further comprising a top edge;
the left shoulder measuring strap comprising a left strap body, at least one left loop-forming strap buckle, at least one left strap indicator, and a plurality of left strap markers;
the top edge and the base edge being positioned opposite to each other across the cup body;
the left wing clampable slider being positioned in between the left band end and the distal lateral edge of the left cup-measuring mechanism;
the left wing clampable slider being slidably connected along the measurement band;
the left shoulder measuring strap being connected in between the left wing clampable slider and the top edge of the left cup-measuring mechanism;
the at least one left loop-forming strap buckle being slidably engaged along the left strap body;
the at least one left strap indicator being integrated into the at least one left loop-forming strap buckle; and,
the plurality of left strap markers being inscribed along the left strap body.

20. The bra gauging device as claimed in claim 15 further comprises:
a right shoulder measuring strap;
a right wing clampable slider;
the cup body further comprising a top edge;
the right shoulder measuring strap comprising a right strap body, at least one right loop-forming strap buckle, at least one right strap indicator, and a plurality of right strap markers;
the top edge and the base edge being positioned opposite to each other across the cup body;
the right wing clampable slider being positioned in between the right band end and the distal lateral edge of the right cup-measuring mechanism;
the right wing clampable slider being slidably connected along the measurement band;
the right shoulder measuring strap being connected in between the right wing clampable slider and the top edge of the right cup-measuring mechanism;
the at least one right loop-forming strap buckle being slidably engaged along the right strap body;
the at least one right strap indicator being integrated into the at least one right loop-forming strap buckle; and,
the plurality of right strap markers being inscribed along the right strap body.

* * * * *